United States Patent [19]

Howard et al.

[11] Patent Number: 5,502,972

[45] Date of Patent: *Apr. 2, 1996

[54] MIXED REFRIGERANT CYCLE FOR ETHYLENE RECOVERY

[75] Inventors: Lee J. Howard, Allentown; Howard C. Rowles, Center Valley, both of Pa.

[73] Assignee: Air Products and Chemicals, Inc., Allentown, Pa.

[*] Notice: The term of this patent shall not extend beyond the expiration date of Pat. No. 5,379,597.

[21] Appl. No.: 289,872

[22] Filed: Aug. 12, 1994

Related U.S. Application Data

[63] Continuation-in-part of Ser. No. 192,024, Feb. 4, 1994, Pat. No. 5,379,597.

[51] Int. Cl.⁶ ............................................. F25J 3/06
[52] U.S. Cl. .............................................. 62/23; 62/40
[58] Field of Search ...................................... 62/23, 40

[56] References Cited

U.S. PATENT DOCUMENTS

| | | | |
|---|---|---|---|
| 3,675,435 | 7/1972 | Jackson et al. | 62/26 |
| 3,932,156 | 1/1976 | Stern | 62/23 |
| 4,002,042 | 1/1977 | Pryor et al. | 62/28 |
| 4,072,485 | 2/1978 | Becdelievre et al. | 62/23 |
| 4,163,652 | 8/1979 | Gazzi et al. | 62/28 |
| 4,629,484 | 12/1986 | Kister | 62/29 |
| 4,720,293 | 1/1988 | Rowles et al. | 62/24 |
| 4,900,347 | 2/1990 | McCue, Jr. et al. | 62/24 |
| 5,035,732 | 7/1991 | McCue, Jr. | 62/24 |
| 5,157,925 | 10/1992 | Denton | 62/23 |

OTHER PUBLICATIONS

Kaiser, V. et al. "Mixed Refrigerant for Ethylene." *Hydrocarbon Processing* Oct. 1976: 129–31.

*Primary Examiner*—Ronald C. Capossela
*Attorney, Agent, or Firm*—John M. Fernbacher

[57] ABSTRACT

A closed-loop mixed refrigerant cycle provides efficient low-level refrigeration for recovering ethylene from a mixed gas feed. Compressed mixed refrigerant vapor is condensed at –20° F. to –50° F. and is subcooled to –175° F. to –225° F. by indirect heat exchange with cold $H_2$, methane, and expander streams from elsewhere in the ethylene plant. A portion of the subcooled refrigerant may be flashed to provide additional subcooling of the main mixed refrigerant stream. Subcooled mixed refrigerant is subsequently flashed to provide very low temperature level refrigeration for feed condensation and demethanizer overhead condenser duties. The invention allows advantageous operation of the feed chilling train at pressures between 150 and 400 psia.

20 Claims, 2 Drawing Sheets

5,502,972

MIXED REFRIGERANT CYCLE FOR ETHYLENE RECOVERY

This is a Continuation-in-Part of Ser. No. 08/192,024 filed Feb. 4, 1994.

FIELD OF THE INVENTION

This invention pertains to the recovery of ethylene from light gases at low temperature, and in particular to an improved mixed refrigerant cycle to provide more efficient refrigeration for such recovery.

BACKGROUND OF THE INVENTION

The recovery of ethylene from crude light hydrocarbon gas mixtures is an economically important but highly energy intensive process. Cryogenic separation methods are commonly used which require large amounts of refrigeration at low temperatures, and the continuing development of methods to reduce net power to provide this refrigeration is important in the petrochemical industry.

Ethylene is recovered from light gas mixtures such as cracked gas from hydrocarbon crackers which contain various concentrations of hydrogen, methane, ethane, ethylene, propane, propylene, and minor amounts of higher hydrocarbons, nitrogen, and other trace components. Refrigeration for condensing and fractionating such mixtures is commonly provided at successively lower temperature levels by ambient cooling water, closed cycle propylene and ethylene systems, and work expansion or Joule-Thomson expansion of pressurized light gases produced in the separation process. Numerous designs have been developed over the years using these types of refrigeration as characterized in representative U.S. Pat. 3,675,435, 4,002,042, 4,163,652, 4,629,484, 4,900,347, and 5,035,732.

The use of closed cycle mixed refrigerant systems can be integrated with one or more of the above-mentioned refrigeration methods to improve the overall energy efficiency of ethylene recovery. Mixed refrigerants for such systems typically comprise methane, ethane, ethylene, propane, propylene, and optionally other light components. Mixed refrigerants exhibit the desirable property of condensing over a range of temperatures, which allows the design of heat exchange systems which are thermodynamically more efficient than single refrigerant systems.

U.S. Pat. No. 4,072,485 describes a mixed refrigerant cycle for providing low level refrigeration in a natural gas processing plant, or in the cryogenic section of an ethylene plant which utilizes one or more partial condensation stages to cool the feed gas. In this cycle, the mixed refrigerant is partially condensed with cooling water or air at near ambient temperature and then totally condensed at +50° F. and subcooled with several levels of propane or propylene refrigeration. In ethylene plant service, the mixed refrigerant is then utilized to provide refrigeration over the temperature range of −40° F. to −148° F.; i.e., it is confined to the same temperature range as the ethylene refrigeration it replaces. A more specific example of this cycle for ethylene plant service is described in an article by Victor Kaiser, et al., "Mixed Refrigerant for Ethylene," in the Oct. 1976 issue of *Hydrocarbon Processing*, pages 129-131.

U.S. Pat. 4,720,293 describes a process for recovering ethylene from refinery off-gas which utilizes a mixed refrigerant cycle. In this process, the mixed refrigerant is utilized in a single heat exchanger over a relatively warm temperature range of +60° F. to −85° F. Refrigeration at lower temperature levels is supplied by vaporization of separated ethane at low partial pressure and high total pressure, and by work expansion of light gases which are typically rejected to fuel along with the ethane.

With the conventional process technology described above, the feed gas chilling and demethanizing must be carried out at pressures in the range of 450 to 650 psia in order to achieve high ethylene recovery (994% or more) because the propylene/ethylene cascade system can provide refrigeration no colder than −150° F. for feed gas chilling and for demethanizer column condenser refrigeration. The amount of refrigeration for feed cooling below −150° F. which can be produced from other process streams in an ethylene plant is limited by operating constraints such as the amount of high pressure hydrogen recovered and the fuel system pressure(s). These constraints limit the amount of expander refrigeration which can be produced, which in turn limits the ethylene recovery. Pressures between 450 and 650 psia are required in the feed gas chilling train and in the demethanizer column so that most of the ethylene can be condensed above −150° F., and so that sufficient fuel gas expansion refrigeration at colder temperatures is available to condense most of the remaining ethylene and achieve low ethylene loss in the demethanizer column overhead vapor.

The integration of improved mixed refrigerant cycles with conventional intermediate and low temperature refrigeration holds promise for further reduction of energy consumption in ethylene recovery. In particular, it is desirable to improve the efficiency of refrigeration at the lowest temperature levels required for high ethylene recovery. The invention described in the following specification and defined in the appended claims provides an improved mixed refrigeration cycle which is particularly advantageous for ethylene recoveries of greater than 99%.

SUMMARY OF THE INVENTION

The recovery of ethylene from a feed gas containing ethylene, hydrogen, and $C_1$ to $C_3$ hydrocarbons includes the steps of compressing the feed gas, cooling the compressed feed gas to condense a portion thereof, fractionating the condensed feed gas liquids in one or more demethanizer columns to recover a light overhead product comprising chiefly hydrogen and methane, and fractionating the demethanizer column bottoms stream to recover an ethylene product and streams containing $C_2$ and heavier hydrocarbons. Typically at least a portion of the hydrogen-methane vapor stream from the final ethylene recovery heat exchanger is sent to a hydrogen recovery section to produce a high-purity hydrogen product and one or more methane-rich streams.

Refrigeration for ethylene recovery is provided in an improved cycle of the present invention which comprises compressing a mixed refrigerant vapor containing two or more components selected from the group consisting of methane, ethane, ethylene, propane, and propylene, and cooling the resulting compressed vapor to yield a condensed mixed refrigerant stream. The condensed mixed refrigerant stream is subcooled by indirect heat exchange with one or more cold process streams to yield a subcooled mixed refrigerant. A first portion of the subcooled mixed refrigerant is flashed and used to provide overhead condenser refrigeration by indirect heat exchange for at least one of the demethanizer columns, which warms and at least partially vaporizes the first portion of subcooled mixed refrigerant. A second portion of the subcooled mixed refrigerant is flashed and the resulting refrigerant provides at least a portion of the refrigeration required for the cooling and partial condensing of the feed gas by indirect heat exchange, which warms and at least partially vaporizes the second portion of subcooled mixed refrigerant. Preferably the feed gas cooling and condensing are accomplished in one or more dephlegmators, but alternatively one or more partial condensers can be utilized. The resulting warmed vapors of the first and second portions of mixed refrigerant are combined and compressed to complete the refrigeration cycle.

One of the cold process streams for mixed refrigerant subcooling may be provided by flashing and vaporizing a third portion of the subcooled mixed refrigerant, and the warmed vapor is combined with the first and second portions of mixed refrigerant to provide mixed refrigerant vapor for compression to complete the refrigeration cycle. Another one or more of the cold process streams can be provided by work expanding the light overhead product from the one or more demethanizer columns and/or any hydrogen and methane which is not processed in the hydrogen recovery section. Additional cold process streams such as the hydrogen and methane-rich streams from the hydrogen recovery section also can be used for mixed refrigerant subcooling.

In an alternative embodiment of the invention, subcooled mixed refrigerant is provided for two feed condensing zones in series in which partially vaporized mixed refrigerant from a cold feed condensing zone provides a portion of the refrigeration to a warm feed condensing zone to provide two condensed feed liquid streams for further separation. Preferably, the two condensing zones utilize dephlegmators, but alternatively can utilize partial condensers. Combinations of partial condensers and dephlegmators may be used; more than two feed condensing zones in series can be used if desired.

A key feature of the present invention is that the feed chilling train and the downstream separation equipment can be operated advantageously in the pressure range of 150 to 400 psia, thereby achieving satisfactory ethylene recovery with lower refrigeration requirements and lower capital costs in the downstream separation equipment.

DETAILED DESCRIPTION OF THE INVENTION

Figure 1:
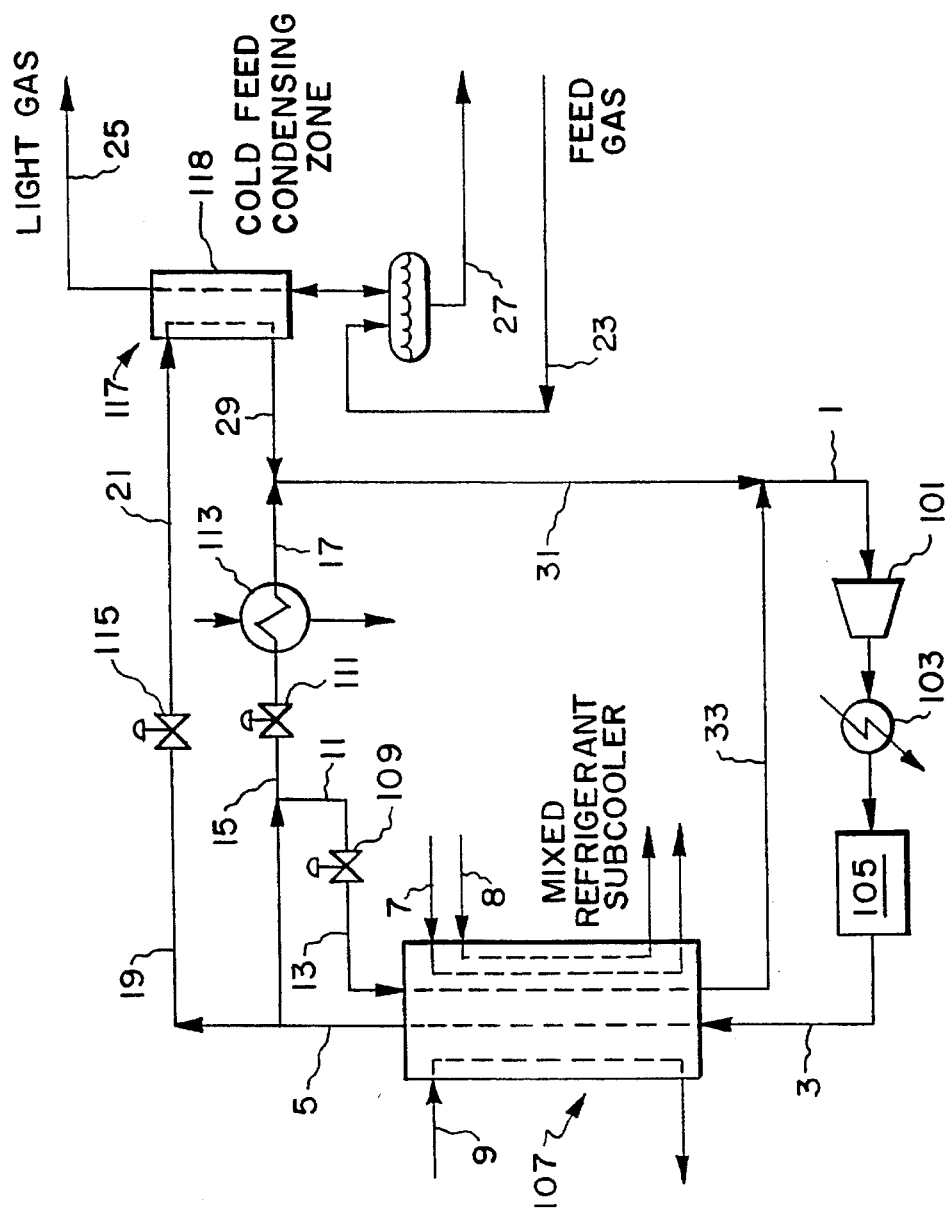
FIG. 1 is a schematic flow diagram of one embodiment of the closed loop mixed refrigerant cycle of the present invention.

In a typical ethylene recovery process, a feed gas comprising hydrogen, methane, ethane, ethylene, propane, propylene, and minor amounts of other light components is compressed, cooled, and partially condensed in single stage condensers or alternatively in one or more dephlegmators which impart several stages of separation during the condensation step. The condensate is separated from lighter gases and is passed to one or more demethanizer columns which recover a light gas overhead comprising chiefly methane and hydrogen, and a bottoms stream rich in $C_2$ and $C_3$ hydrocarbons. This hydrocarbon stream is further fractionated to yield a high purity ethylene product, an ethane-rich byproduct, and a stream of $C_3$ and heavier hydrocarbons.

Essentially all ethylene plants use an ethylene-propylene cascade refrigeration system to provide the major portion of refrigeration required in the ethylene plant. Most of the propylene (high level) refrigeration is utilized at several pressure/temperature levels in the initial feed precooling and fractionation sections of the plant to cool the feed from ambient temperature to about −35° F. and to condense the ethylene refrigerant at about −30° F. Similarly, the ethylene (low level) refrigeration is utilized at several pressure/temperature levels in the cryogenic section of the plant to cool the feed from −35° F. to about −145° F. in order to condense the bulk of the ethylene in the form of liquid feeds to a demethanizer column, and in the demethanizer column overhead condenser at about −150° F. to provide reflux to that column. Ethylene is normally not used to provide refrigeration below −150° F. since that would result in sub-atmospheric pressure at the suction of the ethylene compressor. Refrigeration below −150° F., to condense the remaining ethylene from the feed, is provided primarily by work expansion of rejected light gases, $H_2$ and methane, and/or by vaporization of methane refrigerant which has been condensed by ethylene refrigerant. The work expanded gases are normally used as fuel and consist primarily of the overhead vapor from the demethanizer column, mostly methane, and any uncondensed feed gas, mostly $H_2$ and methane, which is not processed in the $H_2$ recovery section of the ethylene plant.

With the conventional process technology described above, the feed gas chilling and demethanizing must be carried out at pressures in the range of 450 to 650 psia in order to achieve high ethylene recovery (99% or more) because the propylene/ethylene cascade system can provide refrigeration no colder than −150° F. for feed gas chilling and for demethanizer column condenser refrigeration. The amount of refrigeration for feed cooling below −150° F. which can be produced from other process streams in an ethylene plant is limited by operating constraints such as the amount of high pressure hydrogen recovered and the fuel system pressure(s). These constraints limit the amount of expander refrigeration which can be produced, which in turn limits the ethylene recovery. Pressures between 450 and 650 psia are required in the feed gas chilling train and in the demethanizer column so that most of the ethylene can be condensed above −150° F., and so that sufficient fuel gas expansion refrigeration at colder temperatures is available to condense most of the remaining ethylene and achieve low ethylene loss in the demethanizer column overhead vapor.

The present invention utilizes an improved closed-loop mixed refrigerant cycle which provides efficient low-level refrigeration by using the refrigerant in a subcooled state for the demethanizer overhead condenser duty and for feed cooling and condensation. The mixed refrigerant, consisting predominantly of methane, ethane or ethylene and propane or propylene, at a temperature of about −30° F. to −60° F. and 15 to 50 psia (preferably 20 to 35 psia), is compressed to 250 to 500 psia (preferably 300 to 450 psia) and cooled to ambient temperature with cooling water or air with essentially no condensation. The mixed refrigerant vapor is then cooled to about −20° F. to −50° F. using multiple levels of propane or propylene refrigerant to condense at least 80%, and preferably all, of the mixed refrigerant stream. The mixed refrigerant liquid, and vapor if any, is then subcooled to −175° F. to −225° F., with the predominant amount of refrigeration provided by cold $H_2$ and methane streams returning from the $H_2$ recovery section of the ethylene plant and by expanded light gases from the overhead of the demethanizer column and/or uncondensed feed gas which is not processed in the H$_2$ recovery section. These streams will typically be in the range of −175° F. to −235° F. entering the mixed refrigerant subcooler and will be warmed as much as possible for maximum refrigeration recovery. A portion of the subcooled mixed refrigerant liquid may be flashed to low pressure, e.g., 15 to 50 psia, and rewarmed in the mixed refrigerant subcooler, if necessary, to efficiently balance the refrigeration load in the subcooler or to increase the amount of refrigeration produced.

The cooling, condensation, and separation of the feed gas can be operated advantageously in the range of 150 to 400 psia, and the feed gas can be provided in this pressure range as well. Cooling and condensation of the feed gas preferably is accomplished by dephlegmation in a dephlegmator, which is a rectifying heat exchanger which partially condenses and rectifies the feed gas. Typically a dephlegmator yields a degree of separation equivalent to multiple separation stages, typically 5 to 15 stages. Alternatively, cooling and condensation of the feed gas is accomplished in a conventional condenser, defined herein as a partial condenser, in which a feed gas is partially condensed to yield a vapor-liquid mixture which is separated into vapor and liquid streams in a simple separator vessel. A single stage of separation is realized in a partial condenser.

Subcooling of the mixed refrigerant liquid to −175° F. to −225° F. is advantageous in ethylene plants in order to provide sufficiently cold refrigeration to cool the feed gas to −170° F. to −220° F., which is the temperature range required for high (99+%) or ultra-high (99.75+%) ethylene recovery. To attain these high ethylene recoveries, feed gas typically must be cooled to −190° F. to −220° F. in ethylene plants utilizing conventional partial condensation-type heat exchangers or −170° F. to −190° F. in ethylene plants utilizing dephlegmator-type heat exchangers for final feed cooling.

The bulk of the subcooled mixed refrigerant liquid is split into two portions. In one embodiment of the invention, one portion of this refrigerant is flashed to 15 to 50 psia and at least partially vaporized in a cold partial condenser or cold dephlegmator to provide the coldest level of refrigeration, −180° F. to −230° F., for cooling and condensing the feed gas. The remainder of the subcooled mixed refrigerant liquid is flashed to 15 to 50 psia and at least partially vaporized in the demethanizer column overhead condenser to provide reflux to that column. These two mixed refrigerant streams, at about −100° F. to −150° F., are combined and further warmed and totally vaporized in the warm partial condenser or warm dephlegmator to provide a warmer level of refrigeration for cooling and condensing the feed gas. This warmed mixed refrigerant vapor stream, typically at −30° F. to −60° F., is mixed with the stream of mixed refrigerant vaporized in the mixed refrigerant subcooler, if any, and returned to the mixed refrigerant compressor at 15 to 50 psia (preferably 20 to 35 psia).

It is critical to provide refrigeration with the mixed refrigerant cycle at much lower temperatures than the −150° F. level attainable with a conventional ethylene refrigeration cycle, since the amount of refrigeration below −150° F. available from other process streams in the ethylene plant for feed cooling is limited by operating constraints such as the amount of high pressure H$_2$ recovered and the fuel system pressure(s). These constraints limit the amount of expander refrigeration which can be produced, which in turn limits the ethylene recovery. With the mixed refrigerant cycle of the present invention, however, the amount of refrigeration and the coldest temperature level at which it can be provided are not limited by these constraints, and higher levels of ethylene recovery can be attained. Additional and/or colder refrigeration can be provided by the mixed refrigerant cycle by increasing the amount of low pressure mixed refrigerant which is used to subcool the high pressure mixed refrigerant liquid. In addition, the mixed refrigerant cycle can provide refrigeration colder than the −150° F. level normally supplied to the demethanizer column overhead condenser by an ethylene refrigeration cycle. This colder refrigeration can reduce the amount of ethylene lost in the overhead of the demethanizer column and further increase ethylene recovery.

With a propylene/mixed refrigerant cascade system, using the closed-loop mixed refrigerant cycle of the present invention, the amount of refrigeration and the coldest temperature level at which it can be provided are not limited by the amount of high pressure H$_2$ recovered or by the fuel system pressure(s). Therefore, high levels of ethylene recovery in the present invention can be achieved with much lower feed gas pressures in the range of 150 to 400 psia. The colder refrigeration provided by the mixed refrigerant cycle can also be used to reduce the amount of ethylene lost in the overhead of the demethanizer column and further increase ethylene recovery. In addition, the colder refrigeration provided by the mixed refrigerant cycle also permits the demethanizer column(s) to be operated at pressures lower than the conventional 400 to 500 psia level required for high ethylene recovery when ethylene refrigeration is utilized as the overhead condenser refrigerant. At lower pressures, for example in the range of 150 to 400 psia, separation of methane and lighter gases from ethylene and heavier hydrocarbons is easier, resulting in lower refrigeration requirements and lower equipment costs in the demethanizer column system.

This low pressure feed gas chilling concept with a propylene/mixed refrigerant system of the present invention can also be used to recover ethylene, ethane and/or heavier hydrocarbons from refinery or petrochemical off-gases. Other refrigerants, such as propane, ammonia or various freons, could be used to supply high-level refrigeration in place of propylene for feed gas precooling and for condensing She mixed refrigerant. An absorption refrigeration system could also be used to supplement any of these high-level refrigerants.

If three or more partial condensers or dephlegmators are used in series rather than two, the refrigeration for the demethanizer column overhead condenser could be provided by a mixed refrigerant stream in 10 parallel with the refrigeration for the intermediate partial condenser(s) or intermediate dephlegmator(s) instead of in parallel with the cold partial condenser or cold dephlegmator, if the required refrigeration temperature levels are more closely matched with such an arrangement. Obviously, combinations of one or more partial condensers and one or more dephlegmators operated in series also could be used. In addition, the demethanizer column overhead condenser could be replaced with a dephlegmator or could consist of a dephlegmator operating in series with a partial condenser. In either case, refrigeration for these heat exchangers would be provided by the appropriate mixed refrigerant streams of the present invention to best match the temperature levels.

The mixed refrigerant cycle also can be used to recover ethylene, ethane or heavier hydrocarbons from a refinery or petrochemical off-gas. Other refrigerants, such as ammonia or various freons, could be used in place of propane or propylene to supply high level refrigeration for feed gas precooling and for condensing the mixed refrigerant.

The preferred refrigerant composition will depend upon the specific temperature levels at which the refrigeration is provided, the system pressure, and the feed gas composition. Representative refrigerant composition ranges include 5 to 30 mole % methane, 20 to 55 mole % ethylene and/or ethane and 20 to 50 mole % propylene and/or propane. Lower concentrations of light gases, such as hydrogen or nitrogen and heavier hydrocarbons, such as butane, also may be included.

A first embodiment of the invention can be described in detail with reference to FIG. 1. Warm mixed refrigerant vapor I is compressed to 250–500 psia, preferably 300–450 psia, in compressor 101 and cooled against air or cooling water in heat exchanger 103 to ambient temperature. The compressed refrigerant is cooled and condensed, preferably fully condensed, using multiple levels of propane or propylene refrigeration in conventional refrigeration system 105. Condensed mixed refrigerant 3 at −20° to −50° F. is subcooled in mixed refrigerant subcooler 107 to yield subcooled mixed refrigerant 5 at −175° to −225° F. The major portion of subcooling is accomplished by indirect heat exchange with cold process streams 7, 8 and 9 from other parts of the ethylene recovery plant. These cold streams may include work-expanded light gas overhead from the demethanizer column as well as cold methane and hydrogen streams from the hydrogen recovery section of the plant. In addition, a portion 11 of the subcooled mixed refrigerant 5 may be flashed to 15–50 psia across expansion valve 109 and passed through mixed refrigerant subcooler 107 to provide additional refrigeration. The flow of refrigerant portion 11 is controlled to balance the total amount of refrigeration required to subcool the high pressure mixed refrigerant, and to compensate for variations in the properties of cold process streams 7, 8 and 9. Additional cold process streams (not shown) can be used to supplement refrigeration from the described cold process streams 7, 8 and 9. Typically about 80 to 100% of the total refrigeration for heat exchanger 107 is provided by cold process streams and the remainder by flashed subcooled mixed refrigerant 13.

A second portion 15 of subcooled mixed refrigerant 5 is flashed to 15–50 psia across expansion valve 111 to provide refrigeration at −180° F. to −230° F. for demethanizer column overhead condenser 113 to yield mixed refrigerant 17 which is at least partially vaporized. A third portion 19 of subcooled mixed refrigerant 5 is flashed to 15–50 psia across expansion valve 115 to provide refrigeration at −180° F. to −230° F. as stream 21 for cooling and partially condensing feed gas 23 at pressures as low as 150 psia. This is accomplished in cold feed condensing zone 117 to yield light gas stream 25 and liquid condensate 27 which provides feed to a demethanizer column (not shown). Preferably cold dephlegmator 118 is utilized for feed condensation, which yields several stages of rectification and thereby reduces the separation duty of the demethanizer column. Alternatively, a conventional partial condenser can be used instead of cold dephlegmator 118. Refrigerant streams 17 and 29 are combined to form refrigerant stream 31 at about −30° F. to −60° F., which in turn is combined with vaporized mixed refrigerant 33 from mixed refrigerant subcooler 107 to provide mixed refrigerant stream 1 at 15–50 psia, preferably 20–35 psia, to compressor 101. Any of streams 1, 17, 29, 31 or 33 which is partially vaporized can be utilized elsewhere in the plant to provide additional refrigeration by further vaporization.

Figure 2:
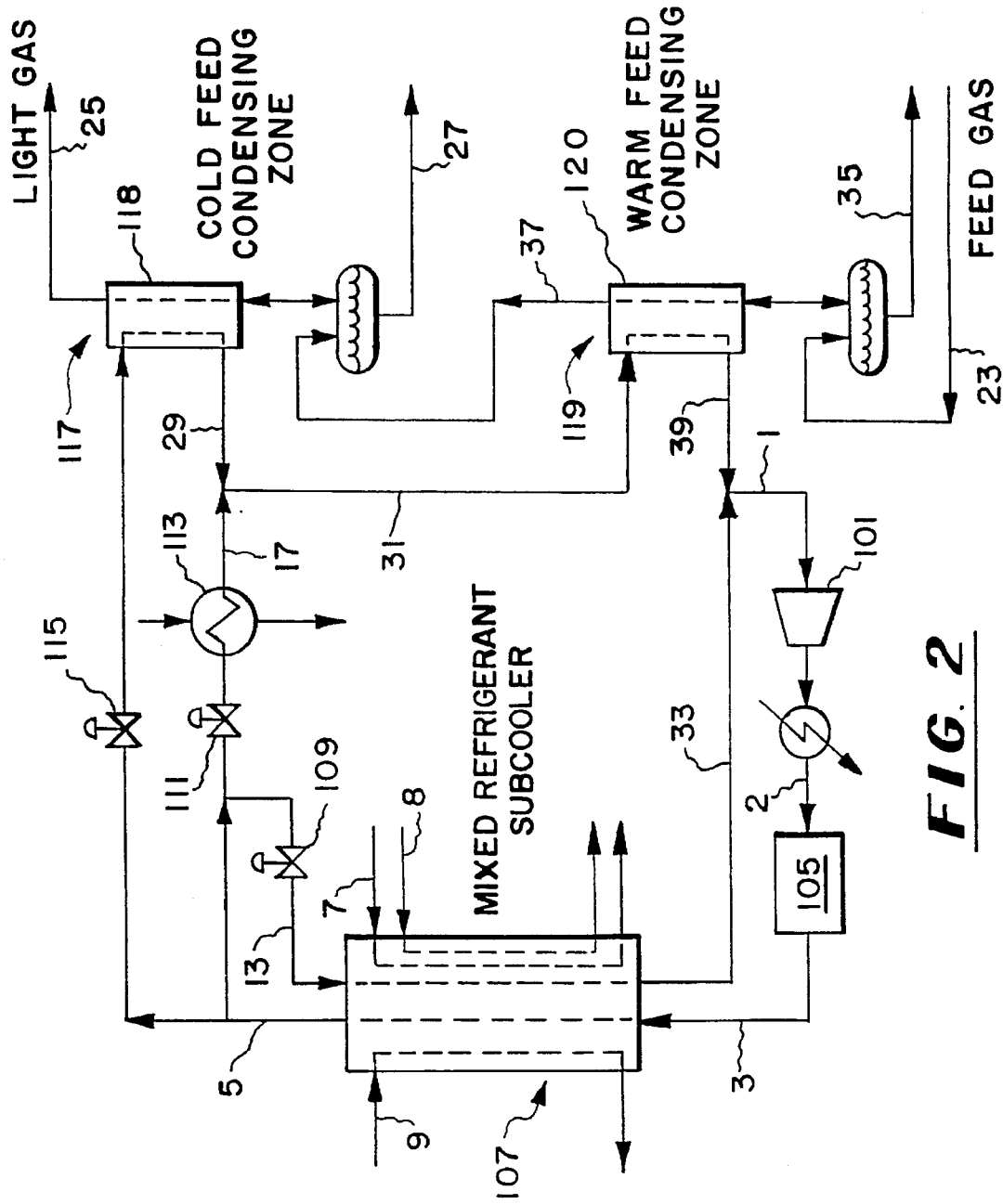
FIG. 2 is a schematic flow diagram of an alternative embodiment of the closed loop mixed refrigerant cycle of the present invention.

An alternative embodiment of the invention is given in FIG. 2 wherein mixed refrigerant is utilized in an additional zone of feed gas cooling and condensation. The mixed refrigerant cycle is similar to that of the embodiment described above for FIG. 1. In this alternative embodiment, refrigeration is provided to demethanizer column condenser 113 and cold feed condensing zone 117 such that combined mixed refrigerant stream 31 is at about −100° F. to −150° F. and is partially vaporized. Feed gas 23 is initially cooled and condensed, at pressures as low as 150 psia, by utilizing mixed refrigerant stream 31 in warm feed condensing zone 119 to yield warm condensed feed liquid 35 and intermediate vapor stream 37 which provides the feed to cold feed condensing zone 117. Preferably, condensing in warm feed condensing zone 119 is accomplished by warm dephlegmator 120. Vaporized mixed refrigerant streams 33 and 39 are combined to yield mixed refrigerant vapor i to compressor 101. The two-step feed gas cooling and condensing by dephlegmators 118 and 120 therefore provide significant prefractionation of the feed into light gas 25, cold condensed feed liquid 27, and warm condensed feed liquid 35. The two condensed feed liquids 27 and 35 can be further fractionated in single or multiple demethanizer columns of reduced size, since significant prefractionation is provided by the two-step dephlegmator system. Alternatively, feed condensing zones 117 and 119 can utilize conventional partial condensers instead of dephlegmators 118 and 120, or a combination of a dephlegmator and a partial condenser can be used.

It is possible to utilize the refrigeration system of the present invention with more than two dephlegmators or partial condensers in series as earlier described. In such an alternative, refrigeration at an intermediate temperature level could be provided in parallel to the intermediate dephlegmator(s) or partial condenser(s) and demethanizer condenser 113. Other arrangements are possible to utilize the subcooled mixed refrigerant of the present invention.

EXAMPLE

Energy and material balances were carried out for the embodiment of FIG. 2 in which mixed refrigerant vapor stream 1 (3102 lb moles per hour) containing 22 vol % methane, 42 vol % ethylene and 36 vol % propylene is compressed from −50° F., 24 psia, to 465 psia and cooled to 100° F. with cooling water. Mixed refrigerant vapor 2 is then cooled to −35° F., 455 psia, with multiple levels of propylene refrigerant in 105 to totally condense the mixed refrigerant stream. The mixed refrigerant liquid 3 is subcooled to −200° F. in mixed refrigerant subcooler 107 against the cold $H_2$, methane, and expander streams 7, 8, and 9 available in the ethylene plant. About 1% of the subcooled mixed refrigerant liquid 5 is flashed to 27 psia across expansion valve 109 to yield refrigerant 13 which is rewarmed to −38° F. in mixed refrigerant subcooler 107 to efficiently balance the refrigeration load for the system. About 32% of subcooled mixed refrigerant liquid 5 is flashed to 30 psia across expansion valve 111, and is partially vaporized and warmed to −125° F. in demethanizer column overhead condenser 113 to provide reflux to that column. The remaining 67% of subcooled mixed refrigerant liquid 5 is flashed to 30 psia across expansion valve 115, and is partially vaporized and warmed to −133° F. in cold dephlegmator 118 to provide refrigeration for cooling and condensing intermediate feed vapor stream 37 from −112° F. to −174° F., corresponding to 99.8% ethylene recovery. That is, 99.8% of the ethylene in feed gas stream 23 is condensed and recovered in the two condensed feed liquid streams 35 and 27, and only 0.2% is lost in the light gas stream 25.

Mixed refrigerant streams 17 and 29 are then combined into stream 31 which is totally vaporized and warmed to −50° F. in warm dephlegmator 120 to provide refrigeration for cooling and condensing feed gas 23 from −33° F. to −112° F. Feed gas 23 (8120 lb moles per hour) containing 24 mole % hydrogen, 38 mole % methane, 31 mole % ethylene, 4 mole % ethane and 3 mole % $C_3$ and heavier hydrocarbons has been precooled to −33° F., 490 psia by a conventional propylene refrigeration system and other refrigerant streams (not shown). Warmed mixed refrigerant stream 39 is mixed with the small stream of mixed refrigerant 33 from mixed refrigerant subcooler 107 and is returned to mixed refrigerant compressor 101 at −50° F. and 24 psia to complete the refrigeration cycle.

In this example, the mixed refrigerant-propylene refrigeration system requires about 204 less compression power at the same ethylene recovery of 99.84 than a conventional ethylene-propylene cascade refrigeration system to supply the same amount of refrigeration for cooling the feed gas from −33° F. to −174° F. In this example, all of the power savings is achieved in the propylene compressor, as a result of shifting much of the low level refrigerant condensing duty from the lowest and most energy intensive level of propylene refrigerant to higher levels. Ethylene refrigerant condenses at a single temperature level, typically −30° F. or −35° F., which concentrates the condensing refrigeration load in the lowest pressure level of propylene refrigerant. The mixed refrigerant condenses over a range of temperature, +75° F. to −35° F. in this example, which spreads the condensing refrigeration load over several pressure levels of propylene refrigerant and significantly reduces the propylene compression power.

With less than a 5% increase in compression power, ethylene recovery could be increased from 99.84 to 99.94 using the mixed refrigerant-propylene refrigeration system. This level of ethylene recovery would not be possible with the ethylene-propylene refrigeration system within the operating constraints of the ethylene plant in this example.

Thus the refrigeration cycle of the present invention uses a subcooled mixed refrigerant to provide refrigeration at temperatures as low as −175° to −225° F. for the recovery of ethylene at high efficiency and reduced power consumption as compared with prior art technology. The distinguishing feature of the invention is that cold process streams and optionally a portion of flashed subcooled mixed refrigerant are used to subcool the high pressure liquified mixed refrigerant, which is subsequently flashed to provide very low level refrigeration for feed condensation and demethanizer column overhead condenser duties. The method of the present invention is a significant improvement over the prior art mixed refrigerant cycles earlier described. The mixed refrigerant cycle described in U.S. Pat. No. 4,072,485 assigned to Technip is intended to provide low level (below −40° F.) refrigeration in a natural gas processing plant or in the cryogenic section of a conventional (cracked gas) ethylene plant, which employs one or more partial condensation stages to cool and condense cracked gas feed to the demethanizer column. In the '485 cycle, the mixed refrigerant is more than half condensed at near ambient temperature with water or air and is totally condensed at +50° F. with one or more levels of warm propane or propylene refrigerant. The mixed refrigerant liquid is subcooled to −26° F. with one or more levels of colder propane or propylene refrigerant. In an ethylene plant application, this subcooled mixed refrigerant liquid is then split into two portions. One portion is further subcooled to −b 58° .F in a "secondary" or "auxiliary" heat exchanger against cold process streams and the remaining portion is further subcooled to −148° F. in the "main" exchanger against returning low pressure mixed refrigerant. The two subcooled mixed refrigerant streams are then combined, flashed to low pressure, and utilized to provide refrigeration over the temperature range of −40° F. to −148° F.; i.e., the mixed refrigerant is confined to exactly the same temperature range as the ethylene refrigeration it replaces. The supply of refrigeration to the demethanizer column overhead condenser in the ethylene plant is not specifically addressed in the '485 patent.

A more specific ethylene plant example of the '485 cycle is described in the earlier-cited article by Kaiser, et al., and indicates a power reduction of 9% for the '485 mixed refrigerant-propylene system as compared to a conventional ethylene-propylene cascade system. This compares to a 20% power reduction in the Example for the mixed refrigerant-propylene system of the present invention. In addition, the '485 example provides for feed gas cooling only to a level of −134° F., which is not sufficient for a modern high-recovery ethylene plant, and does not address the supply of refrigeration to the demethanizer column overhead condenser, which would normally require refrigeration at the −150° F. level. With the '485 mixed refrigerant cycle, ethylene recovery is limited to what could be obtained with the corresponding ethylene refrigeration cycle, which is well below the 99+% ethylene recovery of most modern ethylene plants and far below the 99.75+% ethylene recovery attainable with dephlegmator-type ethylene plants.

The mixed refrigerant cycle of the present invention is particularly well-suited to provide low level refrigeration (below-40° F.) specifically in the cryogenic section of an ethylene plant which uses two or more partial condensation stages, or preferably two or more dephlegmators or combinations of partial condensers and dephlegmators in series, operating below −20° F., to prefractionate the condensing cracked gas feed before it enters the demethanizer column. In this cycle, the mixed refrigerant is at least 804 condensed and preferably totally condensed at −20° F. to −50° F. using one or more levels of propane or propylene refrigerant. The mixed refrigerant liquid is then subcooled to about −200° F. with the major portion of refrigeration provided by cold process streams. None of the mixed refrigerant is subcooled in the feed gas partial condensers or dephlegmators. The low pressure mixed refrigerant streams from the cold dephlegmator and the demethanizer column overhead condenser are then combined and used to provide refrigeration to the intermediate (if any) and warm dephlegmators or partial condensers. Refrigeration for the demethanizer column overhead condenser could alternatively be supplied in parallel with an intermediate dephlegmator or partial condenser.

In the cycle of the present invention, the mixed refrigerant is not totally condensed at +50° F. as in the '485 cycle, since this results in inefficient high pressure levels for the mixed refrigerant stream, e.g., up to 725 psia in the '485 cycle. Instead, the mixed refrigerant of the present invention is at least 80% condensed and preferably totally condensed at −20° F. to −50° F., at pressures below 500 psia. In addition, the mixed refrigerant is subcooled in only one heat exchanger, rather than in both the "auxiliary" and "main" exchangers of '485, which simplifies operation of the cycle. The mixed refrigerant cycle of the present invention also specifically addresses the supply of refrigeration to the demethanizer column overhead condenser, which requires a significant amount of low level (typically −140° F. to −150° F.) refrigeration.

The mixed refrigerant cycle of earlier-cited U.S. Pat. No. 4,720,293 assigned to Air Products and Chemicals, Inc. supplies relatively high level refrigeration (+60 to −85° F.) to a single heat exchanger and relies on vaporization of separated ethane at low partial pressure to provide intermediate level refrigeration (−85° F. to −170° F.), primarily in the demethanizer column overhead condenser. This requires that the separated ethane be combined with the work-expanded $H_2$ and methane (which provide the lowest level refrigeration) and which are then typically sent to fuel after refrigeration recovery. This is highly advantageous in processing refinery off-gases when ethane has no value except as fuel, but would not normally be practical in ethylene plants, where the separated ethane has a higher value as feedstock than as fuel, and must be recycled to the cracking furnaces in a relatively pure state.

In addition to the greater power savings and significantly higher ethylene recovery provided by the mixed refrigerant cycle of the present invention, there are significant capital savings due to the simplification of equipment with the mixed refrigerant cycle, as compared to a conventional ethylene refrigeration cycle. For example, the mixed refrigerant compressor of the present invention has only one suction stream, one suction drum and one recycle control loop. The typical ethylene refrigerant compressor has at 1 east three suction streams, three suction drums and three recycle control loops, a much more expensive arrangement. In addition, the mixed refrigerant compressor of the present invention, with a suction temperature of −50° F. or warmer, can utilize less expensive metallurgy than the ethylene refrigerant compressor, which typically has a suction temperature of −150° F. at the first stage of compression. Compared to the conventional ethylene cycle, there are fewer pieces of equipment and less interconnecting piping with the mixed refrigerant cycle, resulting in lower overall cost.

With the propylene/mixed refrigerant cascade process of the present invention, it is feasible to operate the feed gas chilling train of an ethylene plant or other ethylene recovery unit at about 150 to 400 psia, eliminating one or two stages of feed gas compression and eliminating the associated capital cost of these compression stages. An equivalent amount of compression energy must be added to the propylene and mixed refrigerant compressors, but these are incremental increases in the compression stages, with much smaller associated capital costs. No additional refrigeration compression stages are required.

Feed gas chilling, and optionally demethanizing as well, can be carried out at these lower pressure levels while achieving high ethylene recovery because the propylene/mixed refrigerant cascade system can provide all of the necessary refrigeration at temperatures colder than −150° F., regardless of the amount of expander refrigeration available. The propylene/mixed refrigerant system be supplemented with fuel gas expander refrigeration, but the amount of expander refrigeration is no longer a constraint to ethylene recovery.

An ethylene recovery unit with a low pressure chilling train operating in the range of 150 to 400 psia as described in the present invention provides additional operating benefits compared with conventional operation at higher pressures. These benefits include:

1) less methane and hydrogen are condensed with the ethylene and heavier hydrocarbons, resulting in lower flow rates and lower refrigeration requirements in the demethanizer column(s), 2) more separation of ethylene and ethane is obtained as the feed gas is condensed, particularly where one or more dephlegmators are used in the feed chilling train, resulting in further refrigeration savings in the demethanizer column(s), 3) more hydrogen can be upgraded in purity to a higher value product since it is not necessary to expand some of the hydrogen for low-level refrigeration, producing a lower value fuel, 4) where a multi-zone demethanizer column system is used, more separation of ethylene and ethane in the feed gas chilling section also results in a reduction in the amount of liquid which must be processed in the de-ethanizer column, resulting in a lower flow rate and a savings in separation energy in the de-ethanizer column, 5) where a multi-zone demethanizer column system is used, more separation of ethylene and ethane in the feed gas chilling section also provides more preseparation of the two feed streams to the ethylene/ethane splitter column, resulting in a further savings in separation energy, 6) much of the equipment in the feed pretreatment/drying section, the feed gas chilling train and, optionally, the demethanizer column(s), is operated at significantly lower pressure, resulting in reduced capital cost, and 7) due to the lower pressure ratio between the feed gas and fuel gas, one or more fuel gas expanders are eliminated, further reducing capital cost.

The closed-loop mixed refrigerant cycle utilized in the low pressure chilling train provides low-level refrigeration (below about −40° F.) in the cryogenic section of an ethylene plant which uses multiple partial condensation stages or, preferably, dephlegmators or combinations of partial condensers and dephlegmators in series, operating below about −30° F., to prefractionate the condensing cracked gas feed before it enters the demethanizer column system. Compared to a conventional ethylene refrigeration cycle, the mixed refrigerant cycle provides significant power savings, higher ethylene recovery and also significant capital savings due to the simplification of equipment. For example, the mixed refrigerant compressor has only one suction stream, one suction drum and one recycle control loop. The typical ethylene refrigerant compressor has at least three suction streams, three suction drums and three recycle control loops, a much more expensive arrangement. In addition, the mixed refrigerant compressor, with a suction temperature of −50° F. or warmer, can utilize a cheaper metallurgy than the ethylene refrigerant compressor, which typically has a suction temperature of −150° F. at the first stage of compression. Compared to the conventional refrigerant ethylene cycle, there are fewer pieces of equipment and less interconnecting piping with the mixed refrigerant cycle, resulting in lower overall cost.

The essential characteristics of the present invention are described completely in the foregoing disclosure. One skilled in the art can understand the invention and make various modifications thereto without departing from the basic spirit thereof, and without departing from the scope of the claims which follow.

We claim:

1. In the recovery of ethylene from a feed gas containing ethylene, hydrogen, and $C_1$ to $C_3$ hydrocarbons, wherein said recovery includes the steps of compressing and cooling said feed gas to condense a portion thereof, fractionating the condensed feed gas liquids in one or more demethanizer columns to recover a light overhead product comprising chiefly hydrogen and methane, and fractionating the one or more demethanizer column bottoms streams to recover an ethylene product and streams containing $C_2$ and heavier hydrocarbons, refrigeration for said recovery is provided in a cycle which comprises:

(a) compressing a mixed refrigerant vapor comprising two or more components selected from the group consisting of methane, ethane, ethylene, propane, and propylene, and cooling the resulting compressed vapor to yield a condensed mixed refrigerant stream;

(b) subcooling said condensed mixed refrigerant stream by indirect heat exchange with one or more cold process streams to yield a subcooled mixed refrigerant;

(c) flashing a first portion of said subcooled mixed refrigerant and using the resulting refrigerant to provide overhead condenser refrigeration for at least one of said demethanizer columns by indirect heat exchange, which warms and at least partially vaporizes said first portion of subcooled mixed refrigerant;

(d) flashing a second portion of said subcooled mixed refrigerant and using the resulting refrigerant to provide at least a portion of the refrigeration required to cool said feed gas by indirect heat exchange and condense a portion thereof, which warms and at least partially vaporizes said second portion of subcooled mixed refrigerant; and (e) combining the resulting warmed vapor streams from said first and second portions of the subcooled mixed refrigerants of steps (c) and (d) to provide at least a portion of said mixed refrigerant vapor, and repeating steps (a) through (e);

whereby said feed gas is separated into a vapor stream containing lighter feed components and one or more liquid condensate streams enriched in heavier feed components, wherein the cooling, condensing, and separating of said feed gas is carried out in the pressure range of 150 to 400 psis.

2. The method of claim 1 wherein one of said cold process streams in step (b) is provided by flashing a third portion of said subcooled mixed refrigerant, and wherein the resulting warmed and at least partially vaporized third portion of mixed refrigerant is combined with the first and second portions of mixed refrigerant of steps (c) and (d) to provide said mixed refrigerant vapor of step (a).

3. The method of claim 1 wherein one or more of said cold process streams in step (b) is provided by work expanding said light overhead product from said one or more demethanizer columns.

4. The method of claim 1 wherein one or more of said cold process streams in step (b) is provided by further cooling and partially condensing at least a portion of said vapor stream containing lighter feed components to produce a hydrogen rich vapor stream and one or more methane-rich liquid streams.

5. The method of claim 1 wherein cooling of said feed gas in step (d) by indirect heat exchange with said second portion of mixed refrigerant is accomplished by utilizing at least one dephlegmator or at least one partial condenser or combinations thereof.

6. The method of claim 1 wherein said mixed refrigerant vapor is compressed to about 250–500 psia prior to cooling and condensing.

7. The method of claim 6 wherein said resulting compressed vapor is condensed at least in part at about $-20°$ F. to $-50°$ F. prior to subcooling.

8. The method of claim 6 wherein said condensed mixed refrigerant stream is subcooled to between about $-175°$ F. and $-225°$ F.

9. The method of claim 1 wherein said mixed refrigerant vapor contains 5 to 30 mole % methane, 25 to 55 mole % ethylene, and 25 to 50 mole % propylene.

10. The method of claim 1 wherein said mixed refrigerant vapor contains 5 to 35 mole % methane, 20 to 55 mole % ethane and 20 to 50 mole % propane.

11. In the recovery of ethylene from a feed gas containing ethylene, hydrogen, and $C_1$ to $C_3$ hydrocarbons, wherein said recovery includes the steps of compressing and cooling said feed gas to condense a portion thereof, fractionating the condensed feed gas liquids in one or more demethanizer columns to recover a light overhead product comprising chiefly hydrogen and methane, and fractionating the one or more demethanizer column bottoms streams to recover an ethylene product and streams containing $C_2$ and heavier hydrocarbons, refrigeration for said recovery is provided in a cycle which comprises:

(a) compressing a mixed refrigerant vapor comprising two or more components selected from the group consisting of methane, ethane, ethylene, propane, and propylene, and cooling the resulting compressed vapor to yield a condensed mixed refrigerant stream;

(b) subcooling said condensed mixed refrigerant stream by indirect heat exchange with one or more cold process streams to yield a subcooled mixed refrigerant;

(c) flashing a first portion of said subcooled mixed refrigerant and using the resulting refrigerant to provide overhead condenser refrigeration for at least one of said demethanizer columns by indirect heat exchange, which warms and at least partially vaporizes said first portion of subcooled mixed refrigerant;

(d) flashing a second portion of said subcooled mixed refrigerant and using the resulting refrigerant to cool and condense an intermediate vapor feed stream by indirect heat exchange in a cold feed condensing zone, which warms and at least partially vaporizes said second portion of subcooled mixed refrigerant;

(e) combining the first and second portions of warmed mixed refrigerant of steps (c) and (d), and using at least a portion of the resulting combined mixed refrigerant stream to cool and condense said feed gas by indirect heat exchange in a warm feed condensing zone, which warms and vaporizes said combined mixed refrigerant stream and provides said intermediate vapor feed stream for said cold feed condensing zone of step (d); and (f) returning the resulting vaporized mixed refrigerant stream of step (e) to provide at least a portion of said mixed refrigerant vapor of step (a), and repeating steps (a) through (f);

whereby said feed gas is separated into a vapor stream containing lighter feed components, a cold condensed feed liquid enriched in heavier feed components, and a warm condensed feed liquid further enriched in heavier feed components, wherein the cooling, condensing, and separating of said feed gas is carried out in the pressure range of 150 to 400 psia.

12. The method of claim 11 wherein said cooling and condensation in said warm and cold feed condensing zones is accomplished by at least one dephlegmator, at least one partial condenser, or combinations thereof.

13. The method of claim 11 wherein one of said cold process streams in step (b) is provided by flashing a third portion of said subcooled mixed refrigerant, and wherein the resulting warmed and at least partially vaporized third portion of mixed refrigerant is combined with the first and second portions of mixed refrigerant of steps (c) and (d) to provide said mixed refrigerant vapor of step (a).

14. The method of claim 11 wherein one or more of said cold process streams in step (b) is provided by work expanding said light overhead product from said one or more demethanizer columns.

15. The method of claim 11 wherein one or more of said cold process streams in step (b) is provided by further cooling and partially condensing at least a portion of said vapor stream containing lighter feed components to produce a hydrogen-rich vapor stream and one or more methane-rich liquid streams.

16. The method of claim 11 wherein said mixed refrigerant vapor is compressed to 250–500 psia prior to cooling and condensing.

17. The method of claim 16 wherein said resulting compressed vapor is condensed at least in part at −20° F. to −50° F. prior to subcooling.

18. The method of claim 16 wherein said condensed mixed refrigerant stream is subcooled to between −175° F. and −225° F.

19. The method of claim 11 wherein said mixed refrigerant vapor contains 5 to 30 mole % methane, 25 to 55 mole % ethylene, and 25 to 50 mole % propylene.

20. The method of claim 11 wherein said warm mixed refrigerant vapor contains 5 to 35 mole % methane, 20 to 55 mole % ethane and 20 to 50 mole % propane.

\* \* \* \* \*